(12) United States Patent
Sugizaki (10) Patent No.: US 12,105,072 B2
(45) Date of Patent: Oct. 1, 2024

(54) CHEMICAL SENSOR, DETECTION METHOD, REAGENT AND KIT

(71) Applicant: KABUSHIKI KAISHA TOSHIBA, Tokyo (JP)

(72) Inventor: Yoshiaki Sugizaki, Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 18/301,613

(22) Filed: Apr. 17, 2023

(65) Prior Publication Data

US 2023/0273165 A1 Aug. 31, 2023

Related U.S. Application Data

(62) Division of application No. 16/812,423, filed on Mar. 9, 2020.

(30) Foreign Application Priority Data

Sep. 17, 2019 (JP) .................. 2019-168322

(51) Int. Cl.
*G01N 33/00* (2006.01)
*C12Q 1/00* (2006.01)
*G01N 1/44* (2006.01)
*G01N 27/49* (2006.01)
*G01N 1/28* (2006.01)

(52) U.S. Cl.
CPC ......... *G01N 33/0013* (2013.01); *C12Q 1/005* (2013.01); *G01N 1/44* (2013.01); *G01N 27/49* (2013.01); *G01N 2001/2833* (2013.01); *G01N 33/0042* (2013.01); *G01N 33/0047* (2013.01)

(58) Field of Classification Search
None
See application file for complete search history.

(56) References Cited

U.S. PATENT DOCUMENTS

| | | |
|---|---|---|
| 2010/0106039 A1 | 4/2010 | Abraham-Fuchs et al. |
| 2017/0248565 A1 | 8/2017 | Yamada |
| 2017/0248566 A1 | 8/2017 | Yamada |

(Continued)

FOREIGN PATENT DOCUMENTS

| | | |
|---|---|---|
| JP | 2005-283173 A | 10/2005 |
| JP | 2016-208883 A | 12/2016 |

(Continued)

OTHER PUBLICATIONS

Fujifilm Wako Pure Chemical Corporation, "Nonanal", Aug. 1, 2019, https://labchemwako.fujifilm.com/jp/product/detail/W01W0114-0600.html, 6 pages (with English Machine Translation).

(Continued)

*Primary Examiner* — Daniel S Larkin
(74) *Attorney, Agent, or Firm* — Oblon, McClelland, Maier & Neustadt, L.L.P.

(57) ABSTRACT

According to one embodiment, a chemical sensor includes a sensor element. The sensor element includes a sensitive film and a treatment material. Physical properties of the sensitive film vary as bonding of a target substance to the sensitive film. The sensor element is configured to detect the variation in the physical properties. The treatment material is configured to carry out a treatment onto the target substance before the target substance bonds to the sensitive film.

21 Claims, 4 Drawing Sheets

(56) References Cited

U.S. PATENT DOCUMENTS

2019/0062818 A1    2/2019  Miki
2020/0086323 A1    3/2020  Hongo et al.

FOREIGN PATENT DOCUMENTS

| JP | 2017-156346 A | 9/2017 |
| JP | 2019-41626 A  | 3/2019 |
| JP | 2020-46263 A  | 3/2020 |

OTHER PUBLICATIONS

"Aldehyde oxidase", Wikipedia, the free encyclopedia, Apr. 16, 2013, https://ja.wikipedia.org/wiki/%E3%82%A2%E3%83%AB%E3%83%87%E3%83%92%E3%83%89%E3%82%AA%E3%82%AD%E3%82%B7%E3%83%80%E3%83%BC%E3%82%BC, 4 pages (with English Machine Translation).

"Nonanal", Wikipedia, the free encyclopedia, Sep. 17, 2016, https://ja.wikipedia.org/wiki/%E3%83%8E%E3%83%8A%E3%83%8A%E3%83%BC%E3%83%AB, 4 pages (with English Machine Translation).

CHEMICAL SENSOR, DETECTION METHOD, REAGENT AND KIT

CROSS-REFERENCE TO RELATED APPLICATIONS

This application is a divisional of and claims benefit under 35 U.S.C. § 120 to U.S. application Ser. No. 16/812,423, filed Mar. 9, 2020, now abandoned, which is based upon and claims the benefit of priority under 35 U.S.C. § 119 from Japanese Patent Application No. 2019-168322, filed Sep. 17, 2019, the entire contents of each of which are incorporated herein by reference.3

FIELD

Embodiments described herein relate generally to a chemical sensor, a detection method, a reagent and a kit.

BACKGROUND

There is a demand of detecting a target substance at high sensitivity with a sensor which detects a target substance.

DETAILED DESCRIPTION

In general, according to one embodiment, a chemical sensor includes a sensor element. The sensor element includes a sensitive film and a treatment material. Physical properties of the sensitive film vary as bonding or approachment of a target substance to the sensitive film. The sensor element is configured to detect the variation in the physical properties. The treatment material is configured to carry out a treatment onto the target substance before the target substance bonds to or approaches the sensitive film. The treatment enhances the variation in the physical properties as compared to a case without the treatment.

Various embodiments will be described hereinafter with reference to the accompanying drawings.

First Embodiment

Figure 1:
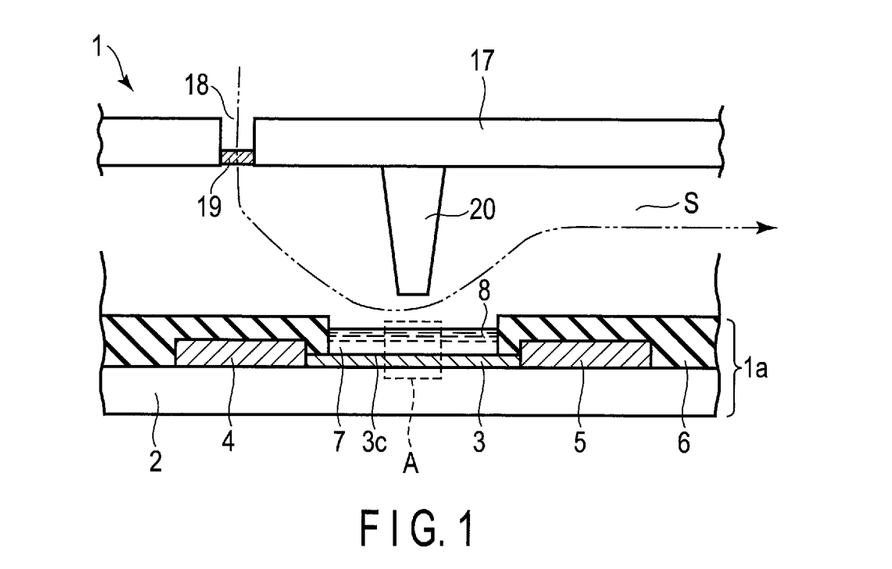
FIG. 1 is a cross section showing an example of a chemical sensor of a first embodiment.

A chemical sensor of the first embodiment is a sensor for detecting a target substance in a Gaseous sample. As shown in FIG. 1, a chemical sensor 1 comprises a sensor element 1a. The sensor element 1a comprises a substrate 2, a film-like sensitive film 3 disposed on a surface of the substrate 2, a first electrode 4 connected to one end of the sensitive film 3, a second electrode 5 connected to the other end, and an insulating layer 6 which covers the first electrode 4 and the second electrode 5. The insulating layer 6 comprises an opening 7 formed therein to expose a partial area of a main surface of the sensitive film 3. On the area of the main surface 3c exposed to the opening 7, a liquid phase 8 formed from a liquid is provided. As will be described later in detail, when a target substance enters the liquid phase 8 and joins with or approaches the sensitive film 3, the physical properties of the sensitive film 3 vary, and the variance in physical properties is detected as a change in value of electric current flowing between the first electrode 4 and the second electrode 5. The physical properties of the sensitive film 3 are, for example, electrical conductivities or an electric resistance value.

In this specification, such an expression as "provided on" a member covers both cases where it is provided in contact with the upper surface of the member or it is provided above the member with a gap therebetween or with some other member interposed therein.

Figure 2:
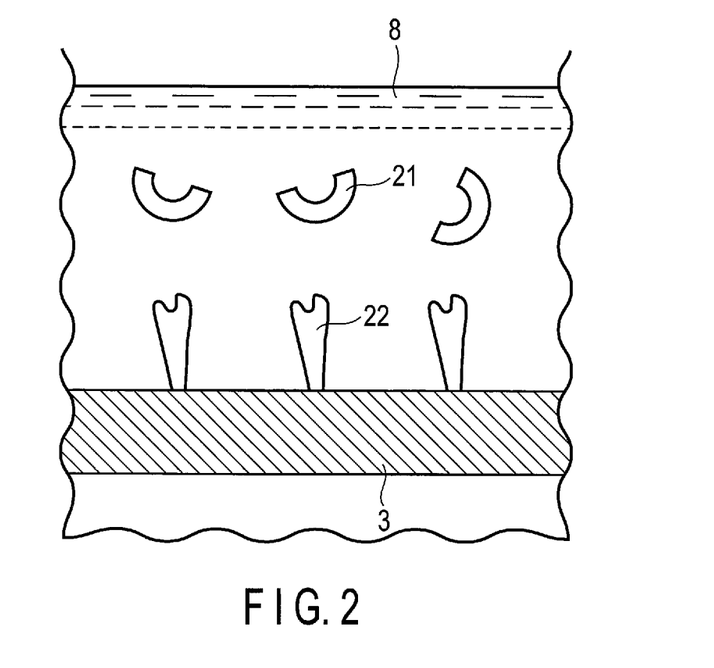
FIG. 2 is an enlarged view of an enclosure A shown in FIG. 1.

The chemical sensor 1 further comprises a treatment material which is configured to carry out a treatment onto a target substance before the target substance joins to or approaches the sensitive film 3. Here, the treatment is referred to as enhancing the variation in physical properties as compared with the case where no treatment is carried out. In the first embodiment, the treatment material is a liquid containing an enzyme. The liquid is disposed on the sensitive film 3 as the liquid phase 8. Therefore, as shown in FIG. 2, which is an enlarged view of the enclosure A in FIG. 1, an enzyme 21 is contained in the liquid phase 8.

The enzyme 21 is an enzyme which has activity to treat a target substance. Here, the treatment is to subject a target substance to chemical change to enhance variation in physical properties of the sensitive film 3 caused when the target substance joins to or approaches the sensitive film 3. Although such treatment is not limited, but it may be, for example, (i) modification of a target substance to produce a hydrogen bond between the target substance and the sensitive film 3; (ii) modification of a target substance to induce π bond interaction between the target substance and the sensitive film 3; (iii) electrostatically charging the target substance; or any combination of these. For example, the treatment may be enhancing the hydrophilic property or polarity of the target substance.

For example, the enzyme 21 has activity for catalyzing a chemical reaction of a target substance, to achieve the treatment. For example, the enzyme 21 has specific or selective catalytic activity to a target substance, and is selected according to the type of the target substance.

Moreover, a trapping body 22 may be fixated on a main surface 3c of the sensitive film 3. The trapping body 22 is a substance to specifically or selectively bind to the pretreated target substance.

Further, the chemical sensor 1 comprises wall portions (not shown) provided to stand on a periphery of the substrate 2, and also a rear surface portion 17 jointed to ends of the wall portions and covering over the sensor element 1a top to define a space S (see FIG. 1).

The rear surface portion 17 comprises a feed opening 18 for gaseous samples, which is a through-hole. To the feed opening 18, a filter 19 is attached to remove contaminants, for example. Moreover, on a surface of the rear surface portion 17, which opposes the opening 7, a guide projection 20 is provided to hang down therefrom. The guide projection 20 guides flow of a gaseous sample allowed to flow in from the feed opening 18 so as to be brought into contact with the liquid phase 8.

With the above-described structure, the gaseous sample flows from the feed opening 18 into the space S between the sensor element 1a and the rear surface portion 17, and then passes through between the guide projection 20 and the sensor element 1a. Thereafter, the gaseous sample flows over the guide projection 20 to a direction opposite to the feed opening 18 (see the arrow in the figure). Further, a fan may be provided in space S so as to make the gaseous sample flow in this direction.

Moreover, the chemical sensor 1 further comprises a power supply (not shown) which impresses voltage between the first electrode 4 and the second electrode 5, and an amperemeter (not shown) which measures a value of electric current flowing between the first electrode 4 and the second electrode 5.

Hereafter, each member of the chemical sensor 1 will be described in detail.

The substrate 2 is, for example, rectangular plate-shaped. The substrate 2 is made from, for example, silicon, glass (SiO or the like), ceramics (SiN or the like) or a polymeric material. The substrate 2 may have a stacking structure in which an insulator layer is provided on a conductor layer. The size of the substrate 2 is not particularly limited, but the thickness of the substrate 2 may be, for example, about 1 mm. As to the length and width, they may be selected so that the substrate has a desired size according to the use of the chemical sensor 1.

The sensitive film 3 is consisted of a material which varies its physical property, for example, electrical conductivity or electric resistance when a material, for example, joins to or approaches the sensitive film 3. Usable examples of the material of the sensitive film 3 are a carbon material, such as graphene, diamond or carbon nanotube, a layered compound, such as molybdenum disulfide ($MoS_2$), tungsten diselenide ($WSe_2$), titanium disulfide ($TiS_2$) or phosphorous (P), or a material electrochemically stable in an oxidation-reduction region of water, such as gold (Au), platinum (Pt) or silver (Ag).

It suffices if the sensitive film 3 is, for example, at least a single-ply atomic layer, but it may be multi-ply. Or the sensitive film 3 may have a shape of a nanowire or a nanotube.

The material of the first electrode 4 and the second electrode 5 is, for example, a metal, such as gold (Au), silver (Ag), copper (Cu), palladium (Pd), platinum (Pt), nickel (Ni), titanium (Ti), chromium (Cr) or aluminum (Al), or a conductive material, such as zinc oxide (ZnO), indium tin oxide (ITO), IGZO or a conductive polymer.

The insulating layer 6 is formed from, for example, an insulating material. The insulating material is, for example, ceramics, such as an oxide film or nitride film, or an insulating polymer, such as polyimide.

The rear surface portion 17 and the guide projection 20 may be, for example, consisted of a material similar to that as the substrate 2, or formed from an inexpensive plastic material or a fluororesin, to which a gaseous sample does not easily attach. The interval between the rear surface portion 17 and the sensor element 1a (the thickness of the space 3) is not particularly limited, but it should preferably be 1 mm to 10 mm.

The filter 19 may be, for example, a filter for coarse dust, which removes dust and dirt. Or, if the contaminant is a specific chemical, a chemical adsorption filter which adsorbs such a chemical may be used as the filter 19. For example, by subjecting the filter 19 to a hydrophilic treatment, hydrophilic contaminants can be removed. When using a sample already known to be contaminant-free or contain such an amount of contaminant that does not affect detection of a target substance, the filter 19 need not be used.

The chemical sensor 1 may be constituted, for example, as a part of a detector which converts variation in a physical property of the sensitive film 3 into an electric signal. The sensor element 1a may have, for example, a structure of a graphene field effect transistor (graphene FET). In that case, the sensitive film 3 is a graphene film and the first electrode 4 is constituted as a source electrode and the second electrode 5 is constituted as a drain electrode. The chemical sensor 1, such as above, may further comprise a gate electrode.

The chemical sensor 1 is not limited to a graphene FET, but may be of a structure of, for example, some other charge detection element, a surface plasmon resonance element (SPR), a surface acoustic wave (SAW) element, a film bulk acoustic resonance (FBAR) element, a quartz crystal microbalance (QCM) element, or a MEMS cantilever element.

The chemical sensor 1, except for the liquid phase 8, can be manufactured by, for example, a semiconductor process.

Examples of the solvent of the liquid reagent which constitutes the liquid phase 8 are water, physiological solution, an ionic liquid, or a PB buffer, a PBS buffer or an organic solvent, such as DMSO or an alcohol, or a mixture of any of those. Moreover, the liquid phase 8 may further contain a solute, such as a pH adjuster, a preservative or a stabilizer.

For example, the thickness of the liquid phase 8 should preferably be greater than 0 μm but 50 μm or less. When the thickness of the liquid phase 8 is 50 μm or less, a target substance 23a can reach the vicinity of the sensitive film 3 in a short time, and can be detected more efficiently. Moreover, with the thickness, denaturation or damage of the trapping body 22, which may occur due to dryness, can be prevented.

The liquid phase 8 does not necessarily have to be provided immediately above the surface 3c of the sensitive film 3, but it should preferably be prepared right above the surface 3c, in which the trapping body 22 can be protected from drying, and further the target substance 23a can be easily carried to the trapping body 22 and/or the sensitive film 3.

Figure 5:
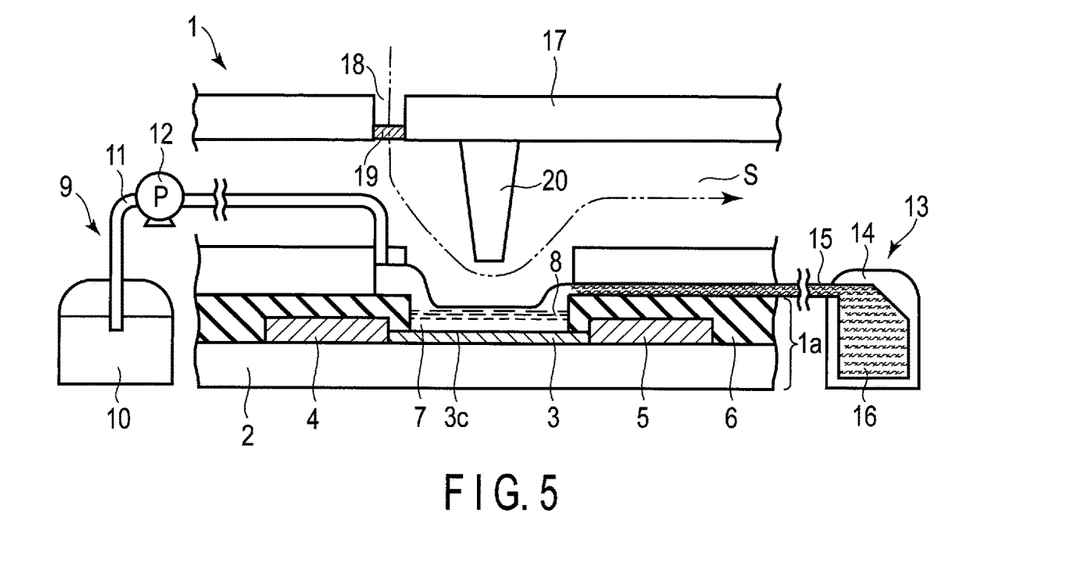
FIG. 5 is a cross section showing an example of a chemical sensor of the first embodiment.

As shown in FIG. 5, the chemical sensor 1 may comprise a liquid supply mechanism 9, which supplies the liquid reagent, which constitutes the liquid phase 8 to the liquid phase 8. The liquid supply mechanism 9 comprises a liquid storage unit 10, which accommodates a liquid reagent, a liquid feed pipe 11 and a pump 12. To the liquid reagent accommodated in the liquid storage unit 10, one end of the liquid feed pipe 11 is inserted. The other end of the liquid feed pipe 11 is in contact with the liquid phase 8. The pump 12 is attached to the liquid feed pipe 11. The liquid sample contains an enzyme 21. Or the enzyme 21 may be fixed onto the sensitive film 3.

Moreover, the chemical sensor 1 may comprise a liquid discharge mechanism 13. The liquid discharge mechanism 13 discharges the liquid reagent of the liquid phase 8 from on the main surface 3c. The liquid discharge mechanism 13 comprises a waste fluid storage unit 14, which accommodates collected waste fluid, a discharge pipe 15, which connects the liquid phase 8 and the waste fluid storage unit 14 to each other, and a water absorption agent 16 accommodated in the waste fluid storage unit 14 and the inside of the waste pipe 15. One end of the water absorption agent 16 is in contact with the liquid phase 8, and the other end is located in the waste fluid storage unit 14. The liquid reagent is absorbed by the water absorption agent 16, and thus it is accommodated in the waste fluid storage unit 14 through the waste pipe 15.

The enzyme 21 is not limited as long as it is of a type subjectable to the treatments (for example, those of (i) to (iii) provided above), and usable examples thereof are oxidoreductase and desaturase.

Here, the treatment (i) which forms a hydrogen bond to the sensitive film 3 may be carried out by, for example, a reaction which substitutes at least some atoms contained in the target substance 23a by some other atoms. For example, the other atoms may be those having electronegativity higher or lower than those of the atoms originally contained in the target substance 23a. Examples of the atoms having a higher electronegativity are a fluorine atom, an oxygen atom, a chlorine atom, a nitrogen atom, and a sulfur atom. When some of these atoms form a hydrogen bond with the sensitive film 3 or the trapping body 22, the amount of variation in physical properties of the sensitive film 3 can be increased.

The treatment (ii) which induces π bond interaction with the sensitive film 3 may be carried out by, for example, a reaction which makes binding between atoms contained in the target substance 23a, by double bonds. In this case, the double bonds may be formed by causing an elimination reaction in the target substance 23a. When these double bonds undergo the π bond interaction with the double bond contained in the sensitive film 3, the amount of variation in physical properties of the sensitive film 3 can be increased. In particular, it is preferable that the sensitive film 3 should be graphene because it can easily induce π bond interaction. The treatment which induces π bond interaction may be carried out by a reaction which forms a triple bond in the target substance 23a.

The treatment (iii) which charges the target substance may be carried out by, for example, an ionization reaction. Here, for example, a functional group which is more easily electrodissociable may be introduced into the target substance 23a, or the target substance 23a may be modified to form a complex ion with a metal ion or the like. For example, when the target substance 23a contains a methyl group, the target substance 23a can be charged by using an enzyme which can change the methyl group into a carboxy group. The target substance 23a which is charged can increase the amount of variation of the sensitive film 3 by electrostatic force, for example. Moreover, with the electrostatic force, the solubility to the liquid phase 8 can be raised.

The enzyme 21 may solely catalyze any of the chemical reactions in the above-described treatments or as a result of catalyzing any of the reactions, any of the other reactions may occur. For example, as a result of the target substance 23a being charged with the enzyme 21, a hydrogen bond may be formed between the target substance 23a and the sensitive film 3. Or as a result of introducing a functional group containing a double bond to the target substance 23a, a hydrogen bond may be formed between the functional group and the sensitive film 3.

The enzyme may be an apoenzyme or may be a holoenzyme. Moreover, as the enzyme 21, such a type may be used that is fixed by a granular fixation method or a liquid fixation method. When the enzyme 21 is an apoenzyme, the liquid phase 8 may also contain a corresponding cofactor. The cofactor is, for example, a coenzyme or a metal ion cofactor.

For example, limonene, of which chemical formula is indicated below, is a low polarity molecule, and it is difficult to detect as it is. When the target substance 23a is limonene, limonene hydroxylase and carveol dehydrogenase can be used as the enzyme 21. In this case, the following chemical reaction may occur.

By limonene hydroxylase and coenzyme $NAD^+$ (or $NADP^+$), the hydrogen atom (—H) bonded with the carbon atom of the phenyl group in the molecule of (+)-limonene is substituted by a hydroxyl group (—OH), and thus (+)-transcarveol is obtained. Moreover, by carveol dehydrogenase and coenzyme $NAD^+$ (or $NADP^+$), the hydroxyl group (—OH) of (+)-transcarveol is substituted by an oxo group (=O), and thus (+)-carvone is obtained. (+)-transcarveol and (+)-carvone can form a hydrogen bond between the sensitive film 3 by a hydroxyl group and an oxo group, respectively.

For example, when the target substance 23a is nonanal, the enzyme 21 should preferably be aldehyde oxidase. In this case, the following chemical reaction occurs.

By aldehyde oxidase, and a coenzyme, namely, flavin adenine dinucleotide (FAD), hemeprotein, molybdoprotein, iron sulfur protein and/or the like, the aldehyde group of the nonanal is substituted by a carboxy group, and thus nonanoic acid is obtained. By the carboxy group, nonanoic acid can form a hydrogen bond with the sensitive film 3.

In the case where the target substance 23a is limonene or nonanal, the chemical reactions may be induced by an enzyme other than those described above. Further, the site of the group where a chemical reaction occurs does not necessarily have to be the position indicated above, or the chemical reactions may occur in different sites.

Moreover, when there are a plurality of kinds of enzymes which can be used for the above described treatment for one kind of target substance 23a, two or more kinds of enzymes may be selected from the plurality of kinds of enzymes, to be used in combination. Moreover, when detecting a plurality of kinds of target substances 23a in one detection operation, the liquid phase 8 may also contain a plurality of kinds of enzymes 21 and cofactors corresponding to the plurality of kinds of target substances 23a.

A preferable example of the enzyme 21 is one having a pocket-like structure, an inside of which is hydrophobic, and an outside of which is hydrophilic. With such a structure, a hydrophobic target substance 23a can easily be captured into the liquid phase 8 by a system shown in FIG. 4.

The trapping body 22 is a substance to specifically or selectively bond to the pre-treated target substance 23b, and it is, for example, a protein, peptide fragment, an antibody, an aptamer, or nucleic acid. With the trapping body 22, it is possible to improve the specificity or selectivity of detection of the target substance 23a. It suffices if the trapping body 22 is fixed to the sensitive film 3 by any well-known method, for example, chemical modification, an interaction or the like.

Figure 3:
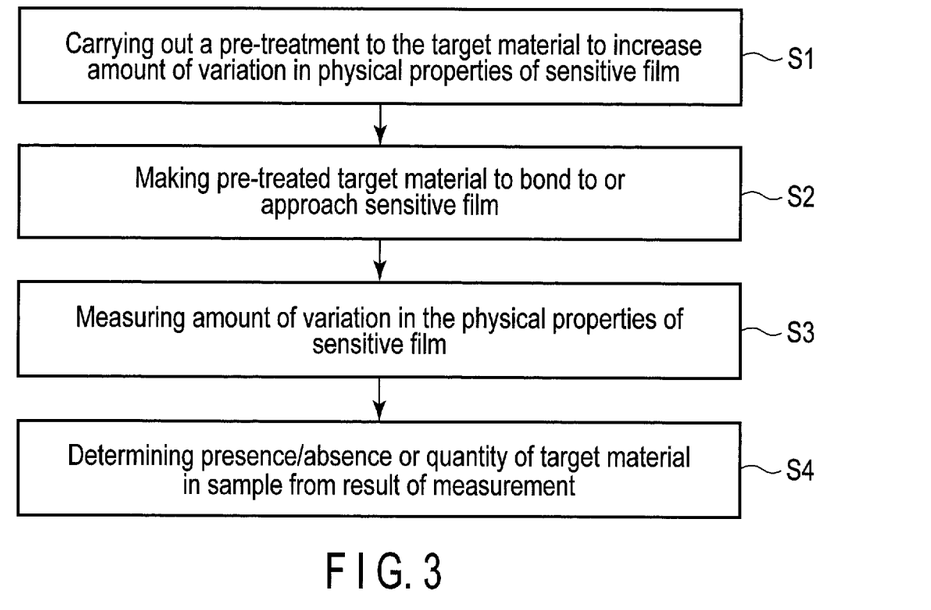
FIG. 3 is a flow chart illustrating an example of a detection method of the first embodiment.

Hereafter, a method of detecting a target substance in a gaseous sample using a chemical sensor 1 will be described. According to the embodiment, the detection method includes the following processing steps, as shown in FIG. 3.
- (S1) A step of carrying out a treatment which increases variation in physical properties of the sensitive film 3 to the target substance;
- (S2) A step of bonding the pre-treated target substance obtained by the treatment or making it closer to the sensitive film 3;
- (S3) A step of detecting the amount of variation in physical properties of the sensitive film 3; and
- (S4) A step of determining the presence/absence or quantity of the target substance in the gaseous sample from the result of the detection.

In one embodiment, steps from S1 to S4 may be continuously carried out without performing another step between any of these steps.

The details of the detection method will now be provided.

The gaseous sample is, for example, a gas expected to contain the target substance. Examples of the gaseous sample are atmospheric air, expired air, or a gas generated from an object to be analyzed, such as a living body or an object, or the surrounding air of an object to be analyzed, but they are not limited thereto.

Examples of the target substance is a material originated from a living body, a material not originated from a living body, an organic compound, an inorganic compound, or a low-molecule compound, and are materials contained in a gas. In particular, examples of the target substances may be an aroma substance, a pheromone, fatty acid, hydrocarbon, a sulfur oxide and a compound, such as synthetic perfume.

Figure 4:
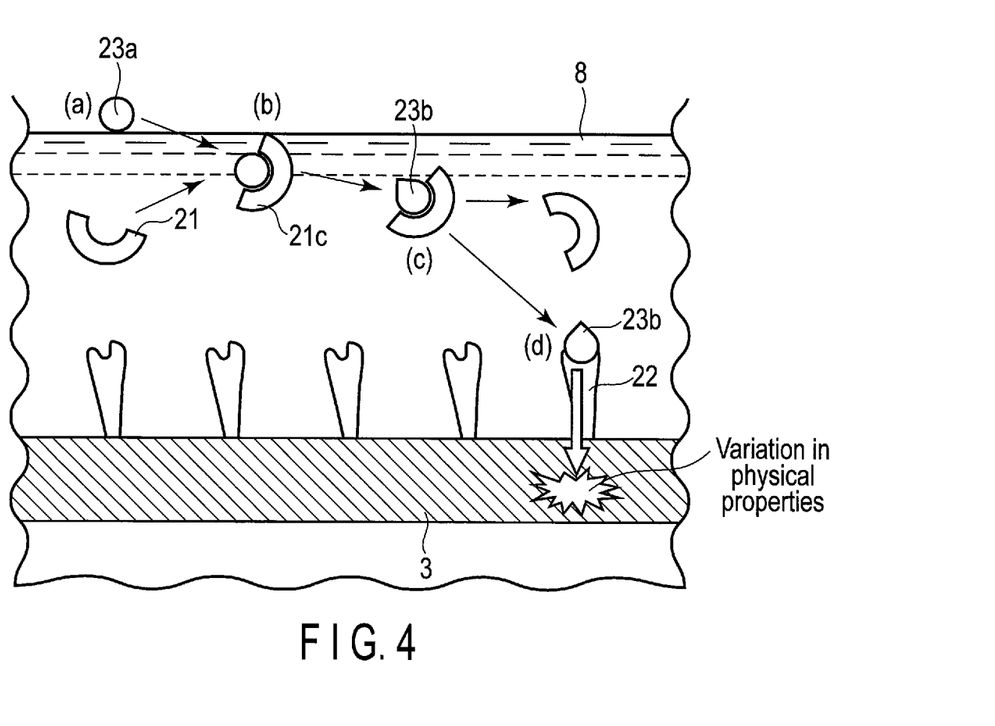
FIG. 4 is a schematic diagram showing an example of the detection method of the first embodiment.

First, a gaseous sample is allowed to flow into a space S from the feed opening 18, and the gaseous sample is brought into contact with the liquid phase 8 which contains the enzyme 21. By the contact, the target substance 23a is brought into contact with the water surface of the liquid phase 8 in a reaction field (a) as shown in FIG. 4. Next, the target substance 23a bonds to the enzyme 21, for example, in the vicinity of the water surface of a reaction field (b), and forms an enzyme-substrate complex 21c. Thus, the target substance 23a is trapped in the liquid phase 8. Next, the chemical reaction of the target substance 23a is catalyzed by the enzyme 21 in a reaction field (c), thereby generating a pre-treated target substance 23b. That is, the target substance 23a is treated by the catalytic activity of the enzyme 21 (Step S1).

The enzyme 21 specifically or selectively catalyzes the reaction with respect to the target substance 23a, and therefore, even if the gaseous sample contains a contaminant, it is possible to specifically treat the target substance 23a, and, as a result, the kinds of products after the treatment can be limited.

The pre-treated target substance 23b is dissociated from the enzyme 21, and is trapped by the trapping body 22 in a reaction field (d), for example, shown in FIG. 4. With the trapping, the pre-treated target substance 23b bonds to the sensitive film 3 via the trapping body 22 and, thus, the pre-treated target substance 23b approaches the sensitive film 3 (Step S2).

As a result, by a hydrogen bond or π bond interaction between the pre-treated target substance 23b and the sensitive film 3, or by the charge on the pre-treated target substance 23b, an electron or a positive hole is supplied to the sensitive film 3, and thus the variation in physical properties of the sensitive film 3 can be increased as compared to the case of mere bonding or approaching of the target substance 23a to the sensitive film of.

The variation in physical properties can be detected as a change in value of electric current flowing between the first electrode 4 and the second electrode 5, for example (Step S3). For example, voltage is impressed between the first electrode 4 and the second electrode 5, and the electric current value is measured with an amperemeter. The measurement of the electric current value is carried out at least two times, before and after supply or the gaseous sample. The measurement may be carried out two times or more, and it is also preferable to monitor from before the supply of the sample up to thereafter.

For example, when there is variation in physical properties of the sensitive film 3 between before and after the supply of the sample, it can be determined that a target substance is present in a gaseous sample. Moreover, according to the amount of variation in physical properties of the sensitive film 3, the quantity of the target substance in the gaseous sample can be determined as well (Step S4).

As the amount of variation in physical properties detected at the Step S3 is greater, the presence/absence and quantity of the target substance 23a can be more clearly determined (that is, the sensitivity is improved). Thus, with the chemical sensor 1, the enzyme 21 carries out such a treatment that makes the target substance enhance the variation in physical properties of the sensitive film 3, and the target substance can be detected at higher sensitivity.

In particular, even if the target substance 23a is a substance difficult as it is to cause variation in physical properties on the sensitive film 3, that is, for example, if it is a highly hydrophobic substance or a substance with less or no polarity, the detection sensitivity of the chemical sensor of the embodiment for such a molecule can be improved by subjecting the substance to the treatment. Moreover, it is difficult to dissolve the target substance 23a of such a type in a polar solvent, but even when a polar solvent is used for the liquid phase 8, by bonding the target substance 23a to the enzyme 21, it can be efficiently trapped into the liquid phase 8. Moreover, even after dissociated from the enzyme 21, the pre-treated target substance 23b can form a hydrogen bond, π interaction or electrostatically bond by a charge between itself and solvent molecules, and therefore it is possible to continuously dissolve it into the liquid phase 8 and, thus, it can bond to or approach the sensitive film 3 efficiently.

Even if the target substance 23a initially forms a hydrogen bond or π interaction with the sensitive film 3, or has a charge, the chemical sensor 1 of the embodiment can further improve the detection sensitivity.

For example, after detection by the chemical sensor 1 is completed, the liquid reagent of the liquid phase 8 is removed from on the main surface 3c by the liquid discharge mechanism 13, and then a new liquid reagent is disposed on the main surface 3c by the liquid supply mechanism 9, thus forming a liquid phase 8. Thus, the target substance 23a is removed from the liquid phase 8, to enable for chemical sensor 1 to detect the target substance 23a again.

Figure 6:
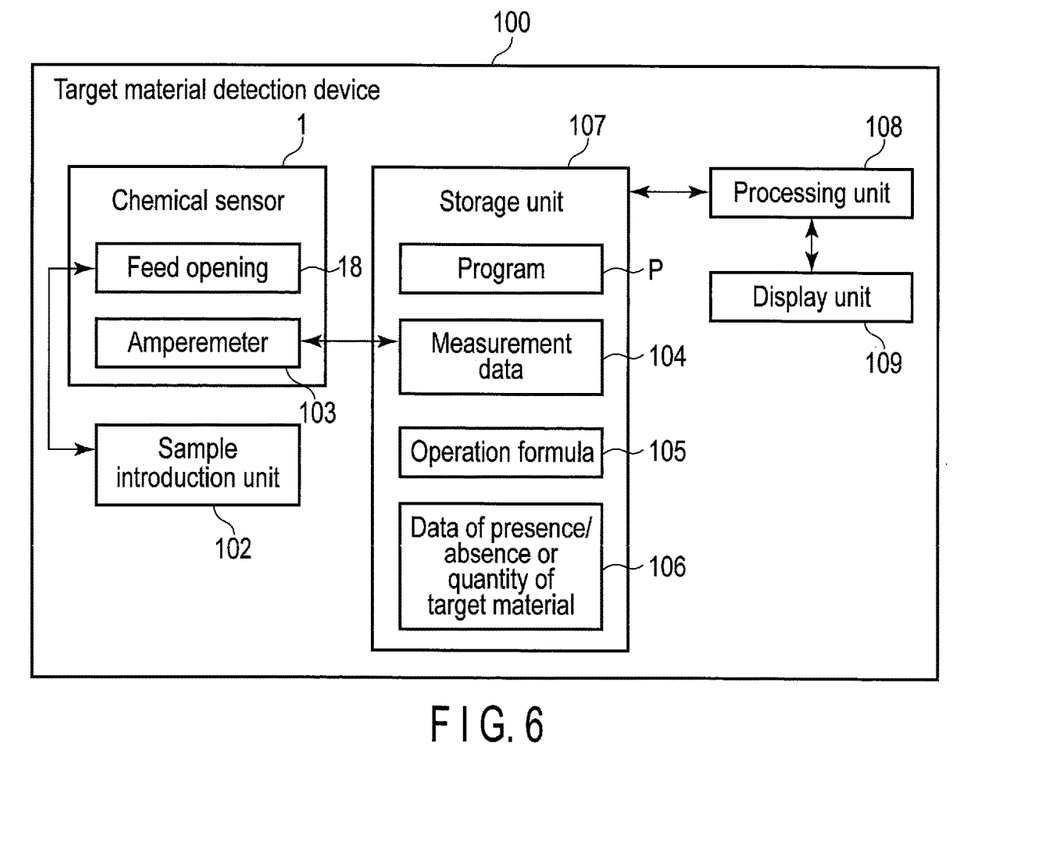
FIG. 6 is a block diagram showing an example of a target substance detection device of the first embodiment.

According to a further embodiment, as shown in FIG. 6, a target substance detection device 100 including a chemical sensor 1 is provided. The target substance detection device 100 includes, for example, a chemical sensor 1; a sample introduction unit 102 which introduces a gaseous sample into a space S from a feed opening 18; a storage unit 107 which stores measurement data 104 on variation in physical properties of the sensitive film 3 measured with an amperemeter 103 of the chemical sensor 1, an operation formula 105 for calculating out the presence/absence or quantity of a target substance in a sample from the data 104, data 106 on the presence/absence or quantity of the target substance, and a program P and the like; a processing unit 108 which calculates out the presence/absence or quantity of the target substance in the sample from the measurement data 104 and the operation formula 105; and a display unit 109.

According to the target substance detection device 100, for example, voltage is impressed between the first electrode 4 and the second electrode 5 of the chemical sensor 1, and a value of electric current flowing between the first electrode 4 and the second electrode 5 is measured with the amperemeter 103 in advance. Next, a gaseous sample is introduced into the space S from the feed opening 18 by the sample introduction unit 102 and the electric current value is measured again after introducing the sample therein. The measurement data 104 of the electric current value is stored in the storage unit 107. Next, the processing unit 108 extracts the measurement data 104 and the operation formula 105 from the storage unit 107, calculates out data 106 on the presence/absence or quantity of the target substance in the sample, and stores it in the storage unit 107. The processing unit 108 gives an instruction to the display unit 109 to display the presence/absence or the quantity of the target substance based on the data 106.

The above-described operation may be performed by entry by the operator to the device, or may be executed by the program P.

Second Embodiment

According to the second embodiment, a reagent is provided for carrying out a treatment which enhances variation in physical properties with respect to a target substance before the target substance bonds to or approaches an sensitive film in the method of detecting the target substance in a gaseous sample using the chemical sensor 1 of the first embodiment.

The reagent contains the enzyme 21 having an activity which carries out treatment onto a target substance. The reagent further contains a cofactor when needed.

The enzyme 21 and cofactor can be contained in an appropriate solvent, to be provided as a liquid reagent. Examples of the solvent are water, physiological solution, an ionic liquid, or a PB buffer, a PBS buffer or an organic solvent, such as DMSO or an alcohol, or a mixture of any of those. The concentration of the enzyme 21 in the liquid reagent is not particularly limited, but it should preferably be higher than or equal to the Michaelis-Menten constant of the enzyme to be used (a substrate concentration which gives a velocity of a half of the maximum velocity), and, for example, several micro-moles (mM).

The enzyme 21 and cofactor may be provided in the form of a powder reagent. In this case, it may be dissolved in any solvent or the like before use, so as to be used as a liquid reagent.

As long as the catalytic activity of the enzyme 21 is not inhibited, the reagent may also contain some other component. Some other component may be, for example, a pH adjuster, a preservative, or a stabilizer. The reagent may be accommodated in an appropriate container to be provided.

The liquid reagent is disposed as the liquid phase 8, for example, on the sensitive film 3 of the chemical sensor 1. When the chemical sensor 1 comprises a liquid supply mechanism 9, the liquid reagent is accommodated in the liquid storage unit 10.

According to a further embodiment, a kit containing the chemical sensor 1 is provided. The kit contains the chemical sensor 1 and the reagent.

Third Embodiment

Figure 7:
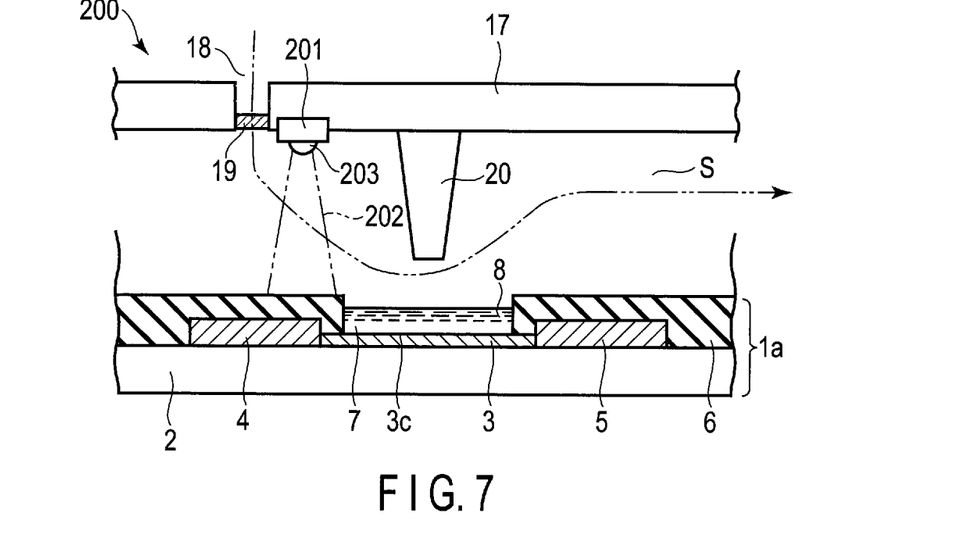
FIG. 7 is a cross section showing an example of a chemical sensor of a third embodiment.

A chemical sensor 200 according to the third embodiment comprises a ultraviolet irradiation device as a treatment material. As shown in FIG. 7, the ultraviolet irradiation device 201 is attached to the rear surface portion 17 near the feed opening 18, In the chemical sensor 200, the enzyme 21 and cofactor are not contained in the liquid phase 8. The rest of the structure is similar to that of the chemical sensor 1 of the first embodiment.

It suffices if the ultraviolet irradiation device 201 has a general structure to generating ultraviolet radiation, and it comprises a light source 203 which generates ultraviolet radiation 202. The light source 203 opposes, for example, the sensor element 1a. As the light source 203, for example, a high-pressure mercury-vapor lamp, a low-pressure mercury lamp, or a metal halide lamp can be used. It is preferable that the wavelength of ultraviolet radiation should be, for example, 185 nm to 400 nm.

The chemical sensor 200 of the third embodiment can as well be used for the detection method explained in the first embodiment shown in FIG. 3. In that case, in Step S1 of the treatment, ultraviolet radiation is irradiated onto the target substance in place of contacting the enzyme with the target substance.

For example, ultraviolet radiation 202 is irradiated by the ultraviolet irradiation device 201 towards a gaseous sample introduced from the feed opening 18 before being brought into contact with the liquid phase 8. The target substance 23a is oxidized by the UV irradiation. By the oxidizing action, chemical reactions (for example, any chemical reaction of items (i) to (iii) set out above), which make the target substance 23a increase variation in physical properties of the sensitive film 3, may occur. The chemical reactions are, for example, those explained in the first embodiment. Thus, the target substance 23a is treated by the chemical reactions.

Steps S2 to S4 can be carried out by methods similar to those explained in the first embodiment.

With the treatment of the third embodiment as well, the variation in physical properties of the sensitive film 3 can be further increased and therefore the target substance 23a can be detected at higher sensitivity. Moreover, the pre-treated target substance 23b is dissolved into the liquid phase 8 easily even when the liquid phase 8 is a polar solvent.

Moreover, according to the chemical sensor 200, treatment can be carried out regardless of the kind of the target substance 23a, and therefore the sensitivity can be more easily improved.

The position where the ultraviolet irradiation device 201 is attached is not limited to that shown in FIG. 7, and as long as ultraviolet radiation can be irradiated onto the target substance 23a before the target substance 23a is brought into contact with the liquid phase 8, it may be disposed at any position of the chemical sensor 200.

For example, the ultraviolet irradiation device 201 is disposed on a side surface of the feed opening 18. In this case, the light source 203 may be disposed so as to irradiate ultraviolet radiation towards the inside of the feed opening 18. Or ultraviolet irradiation device 201 may be attached to a side surface of the guide projection 20, on a side of the feed opening 18.

However, ultraviolet radiation has a possibility for denaturing the trapping body 22, and therefore the ultraviolet irradiation device 201 should preferably be disposed at such a position that ultraviolet radiation is not irradiated on the main surface 3c of the sensitive film 3. In order to avoid undesired influence by ultraviolet radiation, the chemical sensor 1 may comprise a treatment unit located, for example, outside of the space 8, to irradiate UV radiation before the gaseous sample reaches the feed opening 18. The treatment unit comprises another space (for example, a channel) connected with the feed opening 18, other than the space S, and the ultraviolet irradiation device 201 is provided therein to irradiate ultraviolet radiation to the inside thereof. The gaseous sample is, first, stored in the treatment unit, and then, after UV irradiation, it flows into the space S from the feed opening 18.

Fourth Embodiment

Figure 8:
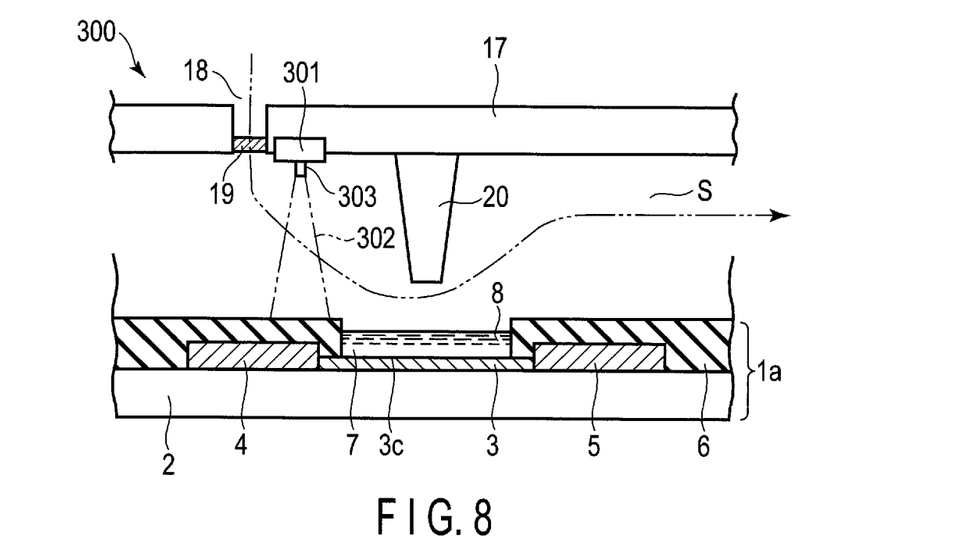
FIG. 8 is a cross section showing an example of a chemical sensor of a fourth embodiment.

A chemical sensor 300 according to the fourth embodiment comprises an ozone generating device as a treatment material. As shown in FIG. 8, the ozone generating device 301 is attached to the rear surface portion 17 near the feed opening 18. In the chemical sensor 300, the liquid phase 8 does not contain an enzyme 21 and cofactor. The rest of the structure is similar to that of the chemical sensor 1 of the first embodiment.

It suffices if the ozone generating device 301 has a general structure to produce ozone. For example, the ozone generating device 301 has an oxygen generating unit, two electrodes and a dielectric material provided therebetween. An alternating current is impressed between both electrodes to cause discharge and oxygen is supplied between the two electrodes, thus producing ozone. The thus produced ozone 302 is emitted from a gas outlet 303. The gas outlet 303 has, for example, a cylindrical shape with an opening formed at the end thereof. The opening opposes the sensor element 1a, and the ozone 302 is emitted towards the gaseous sample before brought into contact with the liquid phase 8.

The chemical sensor 300 of the fourth embodiment can as well be used for the detection method explained in the first embodiment shown in FIG. 3. In that case, in Step S1 of the treatment, ozone is brought into contact with the target substance in place of contacting the enzyme with the target substance.

For example, ozone is emitted by the ozone generating device 301 towards the gaseous sample introduced from the feed opening 18 before being brought into contact with the liquid phase 8. The target substance 23a is oxidized by contacting with the ozone. By the oxidizing action, some chemical reactions (for example, any chemical reaction of items (i) to (iii) set out above), which make the target substance 23a increase variation in physical properties of the sensitive film 3, may occur. The chemical reactions are, for example, those explained in the first embodiment. Thus, the target substance 23a is treated by the chemical reactions.

Steps S2 to S4 can be carried out by methods similar to those explained in the first embodiment.

With the treatment of the fourth embodiment as well, the variation in physical properties of the sensitive film 3 can be further increased and therefore the target substance 23a can be detected at higher sensitivity. Moreover, the pre-treated target substance 23b is dissolved into the liquid phase 8 easily even when the liquid phase 8 is a polar solvent.

Moreover, according to the chemical sensor 300, the treatment can be carried out regardless of the kind of the target substance 23a, and therefore the sensitivity can be more easily improved.

The position where the ozone generating device 301 is attached is not limited to that shown in FIG. 8, and as long as ozone can be brought into contact with the target substance 23a, it may be disposed at any position. For example, the ozone generating device 301 may be attached to the feed opening 18 or the guide projection 20.

The ultraviolet irradiation device 201 of the third embodiment can be used as the ozone generating device 301 of the fourth embodiment. In that case, the ultraviolet wavelength of the light source 203 of the ultraviolet irradiation device 201 should preferably be 185 nm. Moreover, a low pressure mercury lamp or the like may be used as the light source 203.

Moreover, a treatment unit may be provided as in the case of the third embodiment, so as to bring the gaseous sample into contact with ozone in the treatment unit.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A chemical sensor comprising:
a sensor element comprising a sensitive film whose physical properties vary as bonding or approachment of a target substance to the sensitive film,
wherein the sensor element is configured to detect a variation in the physical properties of the sensitive film; and
a treatment material which is configured to carry out a treatment onto the target substance before the target substance bonds to or approaches the sensitive film wherein the treatment material comprises an enzyme having an activity to carry out the treatment onto the target substance and a cofactor of the enzyme,
the treatment enhancing the variation in the physical properties as compared to a case without the treatment.
2. The chemical sensor of claim 1, wherein
the treatment is a modification of the target substance to form a hydrogen bond or cause π bond interaction between itself and the sensitive film, or charging the target substance with a charge.

3. The chemical sensor of claim 1, wherein
the target substance is limonene, the enzyme is limonene hydroxyrase and/or carveol dehydrogenase and the cofactor is NAD+ and/or NADP+.

4. The chemical sensor of claim 1, wherein
the target substance is nonanal, the enzyme is aldehyde oxidase, and the cofactor includes flavin adenine dinucleotide, hemeprotein, molybdoprotein and/or iron sulfur protein.

5. The chemical sensor of claim 1, wherein
the enzyme is contained in a liquid.

6. The chemical sensor of claim 5, wherein
the liquid is provided on the sensitive film.

7. The chemical sensor of claim 6, wherein
the liquid is provided immediately above a surface of the sensitive film, where the target substance bonds or approaches to the sensitive film.

8. The chemical sensor of claim 1, wherein
the target substance is a material contained in a gaseous sample.

9. A kit comprising the chemical sensor of claim 1, a reagent comprising an enzyme having activity to carry out treatment to the target substance and a cofactor of the enzyme.

10. The kit of claim 9, wherein the target substance is limonene, the enzyme is limonene hydroxyrase or carveol dehydrogenase and the cofactor is NAD+ or NADP+.

11. The kit of claim 9, wherein the target substance is nonanal, the enzyme is aldehyde oxidase, and the cofactor includes flavin adenine dinucleotide, hemeprotein, molybdoprotein and/or iron sulfur protein.

12. A chemical sensor comprising:
a sensor element comprising a sensitive film whose physical properties vary as bonding or approachment of a target substance to the sensitive film,
wherein the sensor element is configured to detect a variation in the physical properties;
an enzyme having an activity to carry out a treatment enhances the variation in the physical properties onto the target substance before the target substance bonds to or approaches the sensitive film; and
a cofactor of the enzyme.

13. The chemical sensor of claim 12, wherein the target substance is limonene, the enzyme is limonene hydroxyrase or carveol dehydrogenase and the cofactor is NAD+ or NADP+.

14. The chemical sensor of claim 12, wherein the target substance is nonanal, the enzyme is aldehyde oxidase, and the cofactor includes flavin adenine dinucleotide, hemeprotein, molybdoprotein and/or iron sulfur protein.

15. A method of detecting a target substance in a gaseous sample using a chemical sensor which comprises a chemical sensor element comprising a sensitive film whose physical properties vary as bonding or approachment of the target substance to the sensitive film,
wherein the sensor element is configured to detect a variation in the physical properties,
the method comprising:
carrying out a treatment to the target substance;
making a treated target substance obtained in the treatment to bond to or approach the sensitive film;
detecting an amount of the variation in the physical properties of the sensitive film; and
determining presence/absence or quantity of the target substance in the gaseous sample from a result of the detecting,
wherein
the treatment includes a treatment of the target substance with an enzyme having an activity to carry out the treatment onto the target substance and a cofactor of the enzyme, and
the treatment enhancing the variation in the physical properties of the sensitive film as compared to a case without carrying out the treatment.

16. The method of claim 15, wherein
the treatment is a modification of the target substance to form a hydrogen bond or cause π bond interaction between itself and the sensitive film, or charging the target substance with a charge.

17. The method of claim 15, wherein the target substance is limonene, the enzyme is limonene hydroxyrase or carveol dehydrogenase and the cofactor is NAD+ or NADP+.

18. The method of claim 15, wherein the target substance is nonanal, the enzyme is aldehyde oxidase, and the cofactor includes flavin adenine dinucleotide, hemeprotein, molybdoprotein and/or iron sulfur protein.

19. A reagent to be used for the method of claim 15, comprising an enzyme having an activity to carry out the treatment to the target substance and a cofactor of the enzyme.

20. The reagent of claim 19, wherein
the target substance is limonene, the enzyme is limonene hydroxyrase or carveol dehydrogenase and the cofactor is NAD+ or NADP+.

21. The reagent of claim 19, wherein
the target substance is nonanal, the enzyme is aldehyde oxidase, and the cofactor includes flavin adenine dinucleotide, hemeprotein, molybdoprotein and/or iron sulfur protein.

* * * * *